United States Patent [19]
Klemp

[11] Patent Number: 5,643,243
[45] Date of Patent: Jul. 1, 1997

[54] DISPOSABLE DIAPER WITH CUFF

[75] Inventor: Walter V. Klemp, Houston, Tex.

[73] Assignee: Drypers Corporation, Houston, Tex.

[21] Appl. No.: 519,321

[22] Filed: Aug. 25, 1995

Related U.S. Application Data

[63] Continuation-in-part of Ser. No. 312,334, Sep. 26, 1994, Pat. No. 5,536,350.

[51] Int. Cl.⁶ .............................. A61F 13/15; A61F 13/20
[52] U.S. Cl. ..................... 604/385.2; 604/373; 604/393
[58] Field of Search .................................. 604/358, 373, 604/385.1, 385.2, 393–394

[56] References Cited

U.S. PATENT DOCUMENTS

| | | | |
|---|---|---|---|
| 5,415,644 | 5/1995 | Enloe | 604/385.2 |
| 5,476,458 | 12/1995 | Glaug et al. | 604/385.2 |

*Primary Examiner*—John G. Weiss
*Assistant Examiner*—P. Zuttarelli
*Attorney, Agent, or Firm*—Fulbright & Jaworski

[57] ABSTRACT

A disposable garment having unitary elasticized leg cuffs disposed on the interior surface thereof.

17 Claims, 5 Drawing Sheets

DISPOSABLE DIAPER WITH CUFF

This application is a continuation-in-part of U.S. application Ser. No. 08/312,334, filed Sep. 26, 1994, now U.S. Pat. No. 5,536,350, issued Jul. 16, 1996.

BACKGROUND OF THE INVENTION

This invention generally relates to absorbent articles and, more particularly, to an improved disposable garment for incontinent adults or infants.

Infants and other incontinent persons wear disposable garments to receive and to contain discharge such as feces, urine, and other fluids from the body. Disposable diapers function both to contain the discharged materials and to isolate these materials from the body of the wearer and from the wearer's surroundings. Modern embodiments of disposable diapers perform these tasks in a manner superior to that of traditional cloth diapers.

Prior art disposable diapers disclose three basic structural elements: a fluid permeable topsheet designed to be placed next to the wearer's skin, a backsheet which forms the outer surface of the diaper, and an absorbent element interposed between the topsheet and the backsheet. The topsheet is permeable to fluids. The backsheet is a usually liquid impermeable or repellent. Its function is to contain fluids within the absorbent element thereby protecting the wearer's outer garments and other surfaces from soiling by these fluids. Backsheets are commonly formed of a thin sheet of polyethylene, polypropylene, or other flexible moisture impeding material which is substantially water impervious. The absorbent core of prior art diapers is comprised of a mass of hydrophilic fiber material. These fibers are often formed at least in part from cellulose. The core is intended to absorb fluids that permeate the topsheet. The core is capable of absorbing fluids many times its weight. Disposable diapers are generally hourglass shaped so as to best conform to the body of the wearer. The narrow portion of the shape is placed at the crotch of the wearer and the wide portions of the shape are folded about the body. The wide portions of the shape have projections, called "ears." The diapers are typically secured by tape fasteners attached to the ears.

One of the biggest problems with disposable diapers is designing them so as to comfortably minimize leakage. Many designs have been developed in efforts to satisfy this need. Some prior art disposable diapers have standing inner leg cuffs, combined with elastic leg gatherers, as disclosed, for example, in U.S. Pat. No. 4,704,116 to Enloe. Others have elasticized standing cuffs, combined with elastic leg gatherers, such as disclosed, for example, in U.S. Pat. No. 4,695,278 to Lawson. The leg cuffs and elastic leg gatherers work together to retain waste. Others have "T"-shaped cuffs, such as disclosed, for example, in U.K. Patent Application No. 2 216 393.

The foregoing prior art cuff/elastic gatherer combinations and "T"-shaped cuffs are effective to varying degrees in containing discharge from a wearer's body. However, the designs are generally complex and require multiple steps in fabrication, resulting in undesirable expense and inefficiency. For example, cuff/elastic gather combinations require the creation of both a cuff and an elastic gatherer, which must be separately applied and which must be engineered to work together. "T"-shaped cuffs generally require means to place a "T"-shaped elasticized gasket upon a distal edge of a cuff, which may mean additional engineering and manufacturing expense, resulting in inefficiency.

Additional inefficiencies arise in the construction of garments having an hourglass contoured shape. The contoured garment generally provides a more comfortable fit than traditional rectangular garments. However, in most cases, such contoured garments are quite expensive to produce due to the use of complex high-precision machinery needed to form the intricate shapes. Many such garments are formed from rectangular absorbent articles, often cut in assembly-line fashion from moving webs. To form a garment from a rectangular piece of absorbent material, material is often cut away from the longitudinal edges of the absorbent article and discarded during formation of the leg holes. Such leg-hole cut-outs are known as "noodles." While the contoured garments generally provide a more comfortable fit, they are prone to leakage along the edges of the contoured region.

For the foregoing reasons, there is a need for a disposable garment that is contoured for a comfortable fit, is constructed to prevent leakage, and is efficiently produced. There is also a need for a method of making a disposable garment wherein waste from discarded material used in the process of making the garment is minimized or eliminated.

SUMMARY OF THE INVENTION

To achieve the foregoing objectives, there is disclosed a disposable garment comprising a topsheet; a backsheet; an absorptive core disposed between the topsheet and backsheet; and an elasticized unitary cuff having an (1) edge proximal the disposable garment, the proximal edge attached to or extending from the disposable garment, (2) having an edge distal the disposable garment, (3) positioned to contact a crotch area of a wearer of the disposable garment, and (4) exhibiting planar elastication along a width between the distal edge and proximal edge. The elastication may comprise multiple strands of elastic material. The width of elastication may comprise substantially the distance between the distal edge and the proximal edge. The distal edge of the elasticized unitary cuff may be biased toward a centerline of the disposable garment. The elasticized unitary cuff may have an outboard side and an inboard side, and a portion of one of the sides adhered to the topsheet. The inboard side may be adhered to the topsheet. The unitary cuff may be formed from the topsheet. The unitary cuff may be formed from the backsheet. The elasticized unitary cuff may be attached to the topsheet. The elasticized unitary cuff may be attached to the backsheet.

Also to achieve the objects of the present invention there is disclosed a disposable garment comprising an absorbent pad assembly exhibiting an interior surface, an exterior surface, lateral edges, and longitudinal edges, noodles formed in each longitudinal edge of the absorbent pad assembly and attached at a point proximal to a center point of the absorbent pad assembly, the noodles being folded about the point of attachment and into contact with the interior surface of the absorbent pad assembly, attachment means for securing the folded noodles to the interior surface of the absorbent pad assembly, and cuffs exhibiting a planar elasticating surface, the cuffs formed from or attached to the folded noodles, the cuffs having a distal edge and a proximal edge. The standing cuffs may exhibit elastication along a width between the distal edge and the proximal edge, which width is at least 0.5 inches. The elastication may comprise multiple strands of elastic material. The width of elastication may comprise substantially the distance between the distal edge and the proximal edge. The distal edge of the cuff may be biased toward a centerline of the disposable garment. The elasticized cuff may have an outboard side and an inboard side, and a portion of one of the sides adhered to the topsheet. A portion of the inboard side may be adhered to the topsheet.

DETAILED DESCRIPTION OF THE INVENTION AND PREFERRED EMBODIMENTS

FIGS. 1-8 depict various exemplary embodiments of the claimed invention. Like features in the figures are identified by like numbers.

Figure 1:
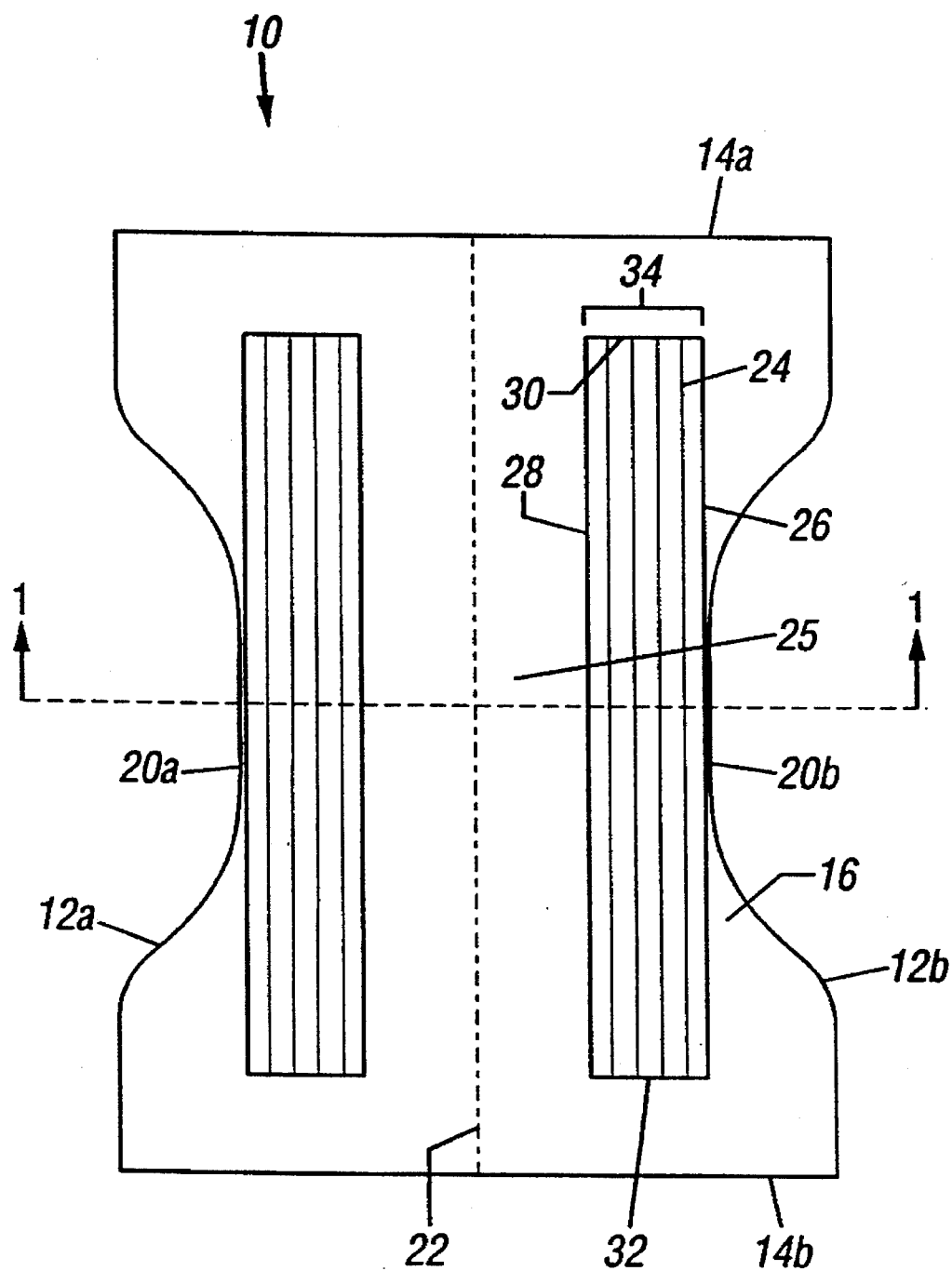
FIG. 1 depicts a top plan view of a disposable garment, in a stretched state, embodying features of the present invention.
Figure 2:
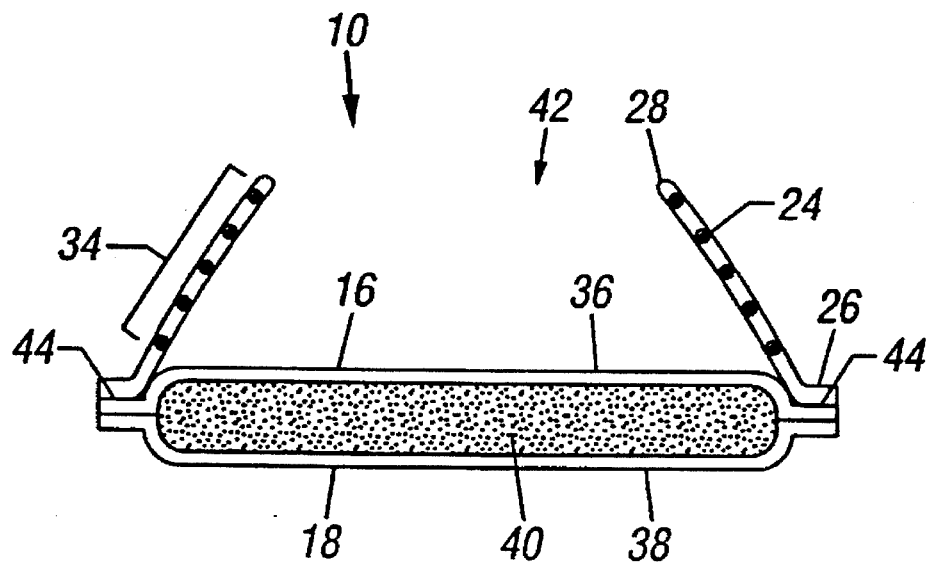
FIG. 2 is a cross-sectional view along lines 1—1 of the disposable garment depicted in FIG. 1.

FIGS. 1-2 depict a disposable garment 10 having longitudinal edges 12a and 12b and lateral edges 14a and 14b. The disposable garment 10 is preferably cut from a continuous web along lateral edges 14a and 14b. The disposable garment 10 exhibits interior surface 16, exterior surface 18, and leg holes 20a and 20b. The disposable garment 10 has a centerline 22 and a crotch area 25.

Disposable garment 10 exhibits elasticized unitary cuffs 24. A disposable garment having such "unitary" cuffs is one which has no elasticized gasketing means outboard the centerline of the crotch area other than the "unitary" cuff. A "unitary" cuff has a proximal edge attached to or made from the disposable garment material, has only one distal edge, and exhibits a planar elasticating surface. A "unitary" cuff is a sole elasticizing means for containing waste from a wearer within the crotch area of a disposable garment.

Elasticized unitary cuffs 24 have a proximal edge 26, a distal edge 28, a first end 30, and a second end 32. The proximal edge 26 is adhered to the disposable garment 10 by any such means known to those skilled in the art, including melting, sonic welding and glue. In the preferred embodiment, elasticized unitary cuffs 24 exhibit planar elastication of at least 0.5 inches between the proximal edge 26 and the distal edge 28, though the entire distance between those edges need not be elasticized. The planar elastication may be any elasticizing means known to those skilled in the art, including solid elasticizing sheets, liquid-applied elastomer, elastomeric thread, or rubber. A series of strands of parallel elastomeric thread 34 is preferred.

It is preferable that the cuffs 24 comprise elasticating and non-elasticating material. Such a combination causes the non-elasticating material to buckle when the elasticating material is in a contracted state, resulting in corrugation of the cuffs. Such corrugation provides the cuffs with structural integrity. Thus, for example, the embodiment of FIGS. 1-2 depicts cuffs comprising a series of parallel elastomic threads disposed with a non-elastomeric fabric. When the elastomic thread is in a contracted state, the corrugation and resulting structural integrity cause the elastomeric threads to act together.

The first and second ends 30 and 32 may be adhered to the disposable garment 10 in order to bias the cuffs 24 when in a contracted state. It is preferable to adhere the inboard sides of the first and second ends 30 and 32 to the topsheet so as to bias the cuffs 24 toward the centerline 22 so as to avoid "seepage." A planar elastic surface biased away from centerline 22 may permit waste material to wedge itself between the wearer's skin and the elastic surface, ultimately escaping the disposable garment. Such wedging between a wearer's skin and an outboard biased, planar elastic surface is "seepage."

FIG. 2 depicts a cross-sectional view along lines 1—1 of the disposable garment depicted in FIG. 1, with the cuffs 24 in a contracted, biased state. The interior surface 16 comprises a top sheet 36 of permeable material. The exterior surface 18 comprises a backsheet 38 of preferably impermeable material. The topsheet 36 and backsheet 38 sandwich an absorbent core 40. The cuffs 24 form a trough 42 for containing waste from a wearer of the disposable garment 10. In the embodiment depicted in FIG. 2, cuffs 24 are separately adhered to the interior surface 16 at points 44.

Figure 3:
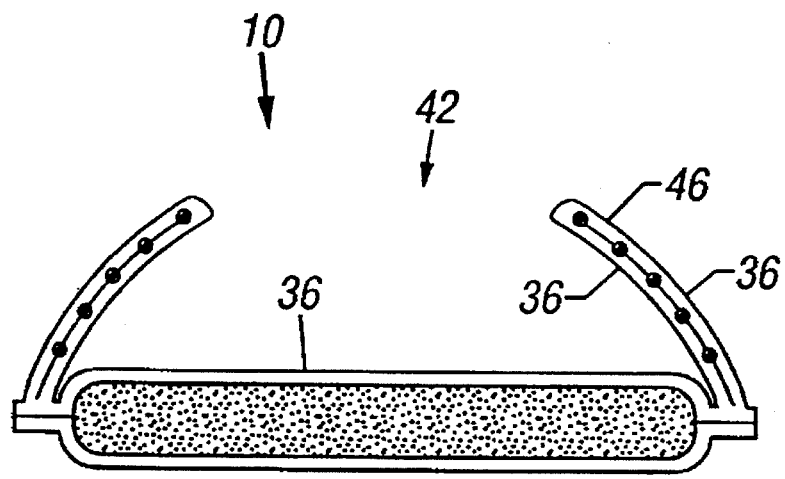
FIG. 3 is a cross-section view of a first alternative embodiment of the present invention.

FIG. 3 depicts a first alternative embodiment of the cuffs depicted in FIG. 2. Elasticized unitary cuffs 46 are formed by making a fold in the topsheet 36. In this embodiment, elastic threads may be sealed within the fold of the topsheet 36. However, the folded topsheet 36 may be elasticized by any means.

Figure 4:
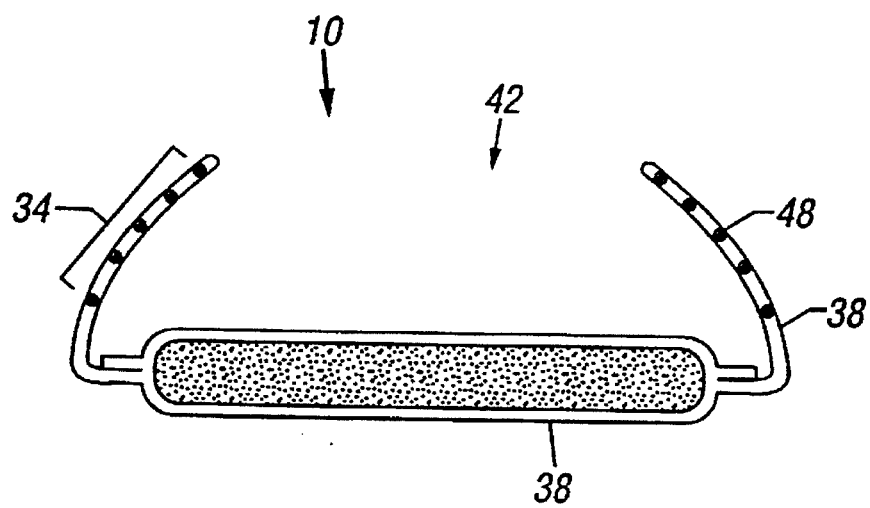
FIG. 4 is a cross-section view of a second alternative embodiment of the present invention.

FIG. 4 depicts a second alternative embodiment of the cuffs depicted in FIG. 2. Elasticized unitary cuffs 48 are formed by an elasticized extension of the backsheet 38 which is folded over the interior surface 16 of the absorbent pad assembly 10.

Figure 5:
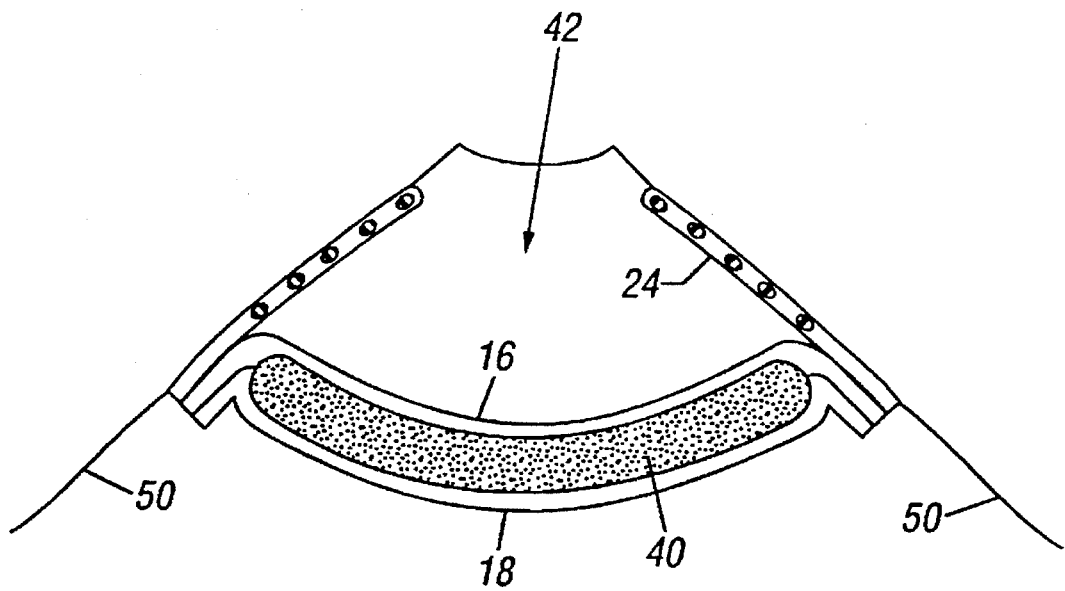
FIG. 5 depicts a cross-sectional view of the disposable garment of FIG. 2 in use by a wearer.

FIG. 5 depicts the disposable garment of FIG. 2 in use on a wearer. Elasticized unitary cuffs 24 form a seal against wearer's legs 50, defining trough 42.

The elasticized unitary cuffs of the present invention may be formed from partially cut noodles, the use of which is generally taught by U.S. Pat. No. 5,536,350, which disclosure is incorporated herein by reference.

Figure 6:
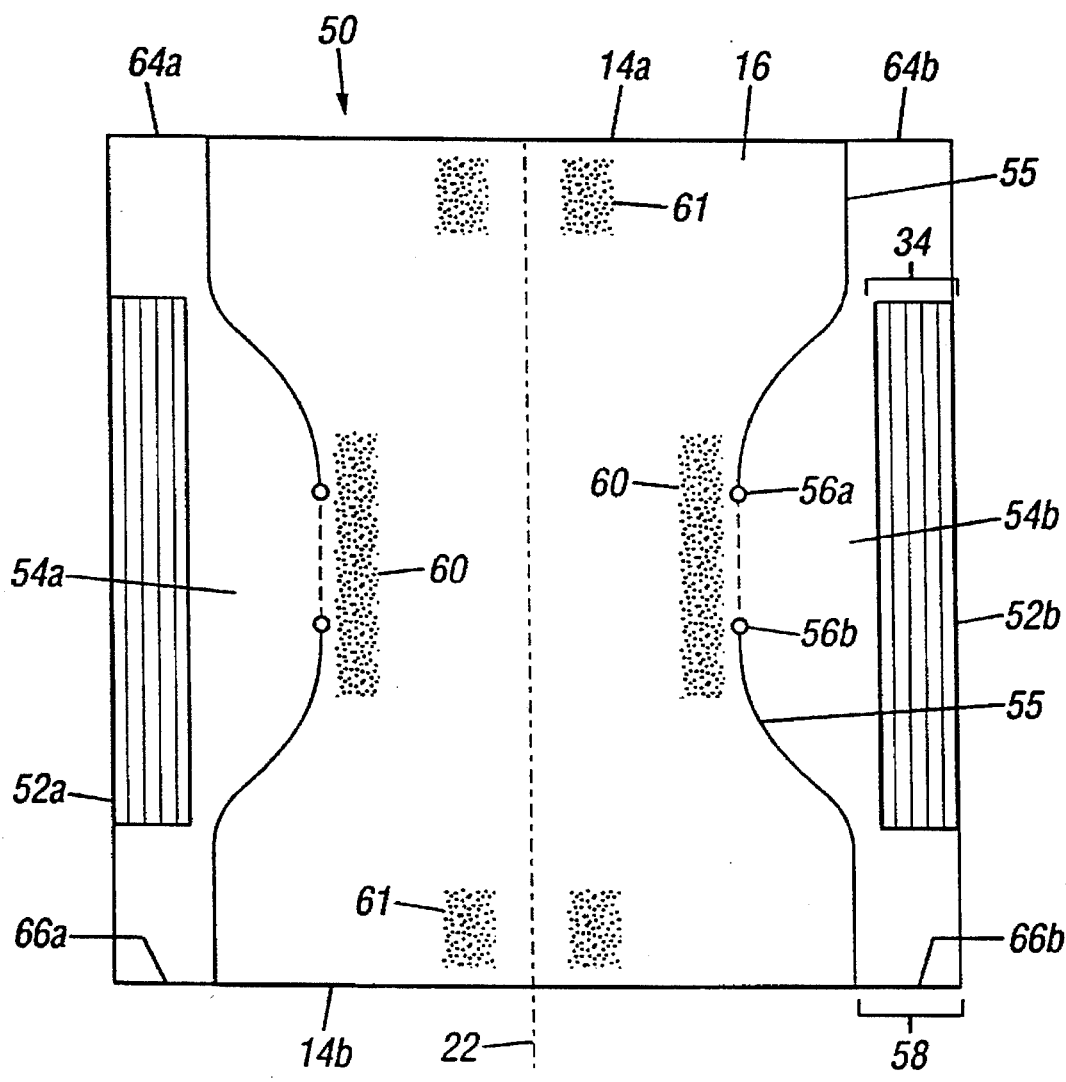
FIG. 6 depicts a top plan view of a third alternative embodiment of the present invention, in a stretched state, prior to the folding of noodles.

FIG. 6 depicts a disposable garment having an absorbent pad assembly 50, preferably exhibiting a rectangular shape, having longitudinal edges 52a and 52b and lateral edges 14a and 14b. The absorbent pad assembly 50 further exhibits an interior surface 16 and an exterior surface 18. The absorbent pad assembly 50 is preferably cut from a continuous web along the lateral edges 14a and 14b.

Partial leg cut-out pieces, or noodles, 54a and 54b are formed in the longitudinal edges 52a and 52b, respectively, of the absorbent pad assembly 50 by partially cutting along a contoured line 55 near the longitudinal edges 52a and 52b of the absorbent pad assembly 50. The noodles are preferably cut from the absorbent pad assembly along the line 55 such that the noodles 54a and 54b remain attached to the absorbent pad assembly 50 between attachment points 56a and 56b, respectively, proximal the center line 22 of the absorbent pad assembly 50. The noodles 54a and 54b are preferably formed before the absorbent pad assembly 50 is cut from the web.

The outer edges of each noodle 54a and 54b exhibit a folding strip 58 which is each preferably formed of the absorbent pad assembly 50 by cutting along the contoured line 55. The folding strip 58 may comprise topsheet, backsheet, or both. The folding strip 58 may extend the longitudinal length of longitudinal edges 52a and 52b, as depicted in FIG. 6, but it may be shorter. Elastic means, such as parallel elastic threads 34, may be applied to or incorporated into the folding strands 58.

The elastic threads 34 may be applied to the folding strip 58 in a continuous fashion with applied adhesive, such as glue. The elastic strands 34 may be applied to either the exterior surface 18 or the interior surface 16 of the absorbent pad assembly 10.

Adhesive may be applied to the interior surface 16 as shown generally by 60. Preferably, adhesive is applied near attachment points 56a and 56b at a location that mirrors the edge of the noodles 54a and 54b. Such application of adhesive facilitates tacking of the noodles 54a and 54b once the noodles are folded toward the centerline 22 of the assembly 50. Adhesive may similarly be applied to the interior surface 16 as shown generally by 61.

Figure 7:
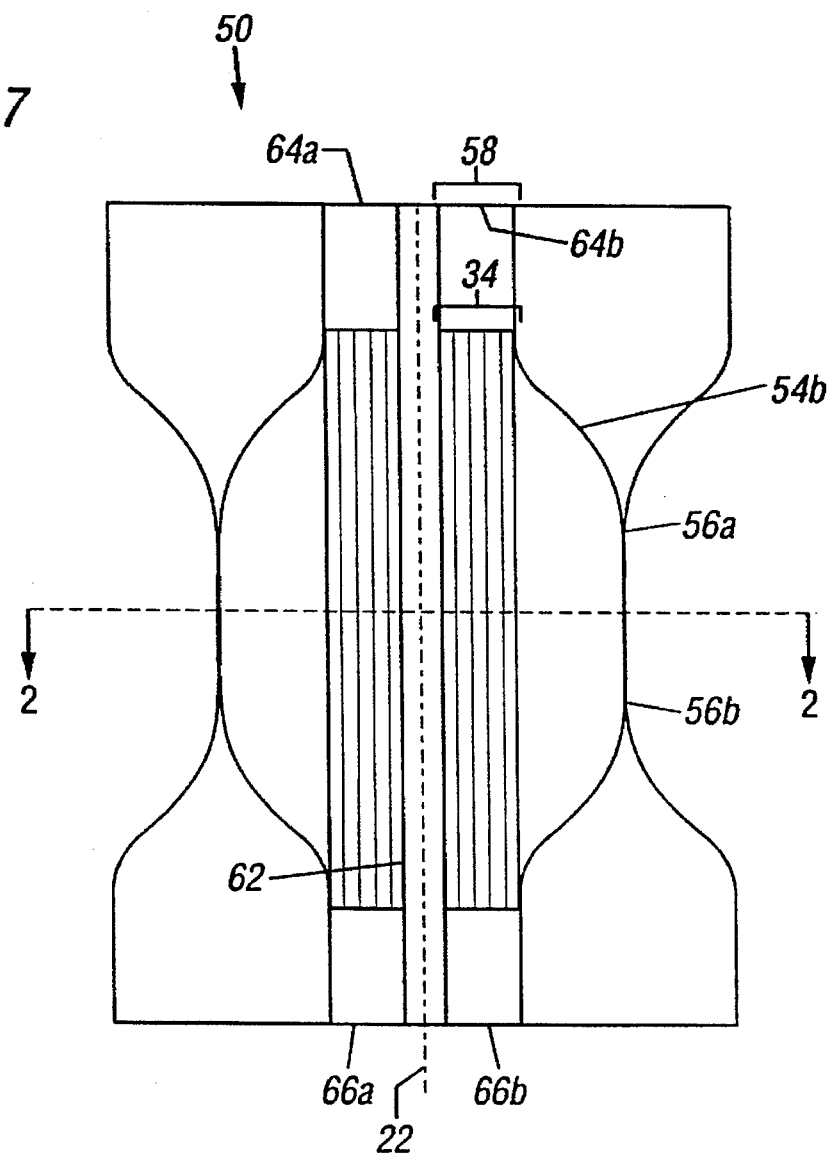
FIG. 7 depicts the disposable garment of FIG. 6, in a stretched state, with the noodles folded.
Figure 8:
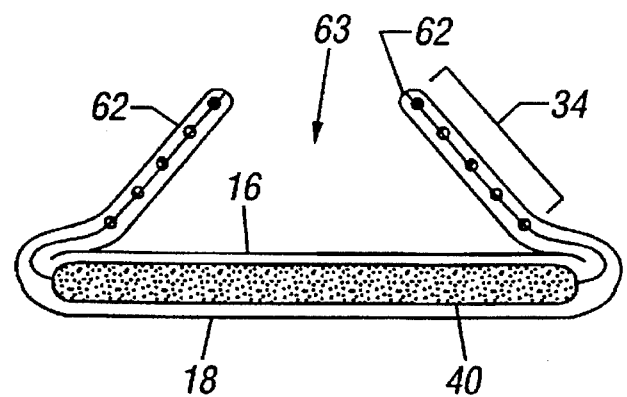
FIG. 8 depicts a cross-sectional view along lines 2—2 of the disposable garment depicted in FIG. 7.

Once the adhesive 60 and 61 has been applied, the noodles 56a and 56b may be folded toward the interior surface 16 and centerline 22 of the assembly 50, whereby the noodles 56a and 56b become tacked to the interior 16 of the assembly 50 as depicted in FIG. 7. First and second edges 64a, 64b, 66a, and 66b may be tacked to the interior surface 16 at adhesive 61 to bias the cuffs 62 inboard toward the centerline 22. Such tacking may be affected by other means, such as melting or sonic welding. The folded noodles 54a and 54b form elasticized standing cuffs 62, defining a trough 63 at the center of the interior surface 16 of the absorbent pad assembly 50.

The illustrated embodiments are examples of the present invention. Various design contours of the cuffs and the noodles, several folding patterns cuffs and for the noodles, and several patterns for adhesive are possible within the scope of the invention. For example, the formation of the cuffs, the folding of the noodles, and the folding of the folding strips may be varied, as may be the location of elastic. Non-elasticized material, such as excess topsheet and backsheet material, may extend outboard of the cuffs, provided such material is not elasticized. It will be apparent to one skilled in the art that many embodiments of the invention are possible within the scope of the claims.

I claim:

1. A disposable garment comprising:
   a topsheet;
   a backsheet;
   an absorptive core disposed between and attached the topsheet and backsheet; and
   an elasticized unitary cuff:
   a) having an edge proximal the topsheet or backsheet, the proximal edge attached to or extending from the topsheet or backsheet;
   b) having an edge distal the topsheet or backsheet;
   c) positioned to contact a crotch area of a wearer of the disposable garment; and
   d) exhibiting planar elastication along a width between the distal edge and proximal edge;
   the elasticized unitary cuff essentially constituting the sole elasticizing means for containing waste from a wearer within a crotch area of the disposable garment.

2. The disposable garment of claim 1 in which the elastication comprises multiple strands of elastic material.

3. The disposable garment of claim 1 in which the width of elastication comprises substantially the distance between the distal edge and the proximal edge.

4. The disposable garment of claim 1 in which the distal edge of the elasticized unitary cuff is biased toward a centerline of the disposable garment.

5. The disposable garment of claim 1 in which the elasticized unitary cuff has an outboard side and an inboard side, and a portion of one of the sides adhered to the topsheet.

6. The disposable garment of claim 5 in which a portion of the inboard side is adhered to the topsheet.

7. The disposable garment of claim 1 in which the elasticized unitary cuff is formed from the topsheet.

8. The disposable garment of claim 1 in which the elasticized unitary cuff is formed from the backsheet.

9. The disposable garment of claim 1 in which the elasticized of the unitary standing cuff is attached to the topsheet.

10. The disposable garment of claim 1 in which the elasticized unitary cuff is attached to the backsheet.

11. A disposable garment comprising:
    an absorbent pad assembly exhibiting an interior surface, an exterior surface, lateral edges, and longitudinal edges;
    noodles formed in each longitudinal edge of the absorbent pad assembly and attached at a point proximal to a center point of the absorbent pad assembly, the noodles being folded about the point of attachment and into contact with the interior surface of the absorbent pad assembly;
    attachment means for securing the folded noodles to the interior surface of the absorbent pad assembly; and
    cuffs exhibiting a planar elasticating surface, the cuffs formed from or attached to the folded noodles, the cuffs having a distal edge and a proximal edge;
    the cuffs essentially constituting the sole elasticizing means for containing waste from a wearer within a crotch area of the disposable garment.

12. The disposable garment of claim 11 in which the cuffs exhibit elastication along a width between the distal edge and the proximal edge, which width is at least 0.5 inches.

13. The disposable garment of claim 12 in which the elastication comprises multiple strands of elastic material.

14. The disposable garment of claim 11 in which the width of elastication comprises substantially the distance between the distal edge and the proximal edge.

15. The disposable garment of claim 11 in which the distal edge of the cuff is biased toward a centerline of the disposable garment.

16. The disposable garment of claim 11 in which the elasticized cuff has an outboard side and an inboard side, and a portion of one of the sides adhered to the topsheet.

17. The disposable garment of claim 16 in which a portion of the inboard side is adhered to the topsheet.

* * * * *